United States Patent
Sorger (10) Patent No.: US 10,405,753 B2
(45) Date of Patent: Sep. 10, 2019

(54) PHARMACEUTICAL COMPOSITIONS OF NEAR IR CLOSED CHAIN, SULFO-CYANINE DYES

(71) Applicant: Intuitive Surgical Operations, Inc., Sunnyvale, CA (US)

(72) Inventor: Jonathan Sorger, Belmont, CA (US)

(73) Assignee: Intuitive Surgical Operations, Inc., Sunnyvale, CA (US)

( * ) Notice: Subject to any disclaimer, the term of this patent is extended or adjusted under 35 U.S.C. 154(b) by 497 days.

(21) Appl. No.: 14/937,641

(22) Filed: Nov. 10, 2015

(65) Prior Publication Data

US 2017/0127948 A1      May 11, 2017

(51) Int. Cl.

| | |
|---|---|
| *A61B 5/00* | (2006.01) |
| *A61B 8/00* | (2006.01) |
| *A61B 10/00* | (2006.01) |
| *A61K 49/06* | (2006.01) |
| *C09B 23/16* | (2006.01) |
| *C09B 23/01* | (2006.01) |
| *C09B 23/08* | (2006.01) |
| *A61K 49/00* | (2006.01) |

(52) U.S. Cl.
CPC ........ *A61B 5/0082* (2013.01); *A61K 49/0032* (2013.01); *A61K 49/06* (2013.01); *C09B 23/0025* (2013.01); *C09B 23/0066* (2013.01); *C09B 23/086* (2013.01); *C09B 23/164* (2013.01); *A61K 49/0017* (2013.01)

(58) Field of Classification Search
None
See application file for complete search history.

(56) References Cited

U.S. PATENT DOCUMENTS

| 5,519,145 A | 5/1996 | Fabricius et al. |
| 7,488,468 B1 * | 2/2009 | Miwa ................ A61K 49/0032 |
| | | 252/301.22 |
| 2017/0283384 A1 * | 10/2017 | Pomper ............... C07D 311/20 |

FOREIGN PATENT DOCUMENTS

| EP | 0753584 A1 | 1/1997 | |
| JP | H06145539 A | 5/1994 | |
| WO | WO-0016810 A1 | 3/2000 | |
| WO | WO 2008/071937 A1 * | 6/2008 | ........... C07D 401/04 |
| WO | WO-2010091243 A1 | 8/2010 | |

OTHER PUBLICATIONS

ThermoFisher Scientific DyLight® 800 free acid Certificate of Analysis, 2012.*
International Search Report and Written Opinion for Application No. PCT/US2016/060671, dated Feb. 27, 2017, 16 pages.
Vertut, Jean and Phillipe Coiffet, Robot Technology: Teleoperation and Robotics Evolution and Development, English translation, Prentice-Hall, Inc., Inglewood Cliffs, NJ, USA 1986, vol. 3A, 332 pages.

* cited by examiner

*Primary Examiner* — Michael G. Hartley
*Assistant Examiner* — Melissa J Perreira (57) ABSTRACT

Sterile and non-toxic pharmaceutical compositions of near IR, closed chain, sulfo-cyanine dyes and methods for visualizing tissue under illumination with near-infrared radiation are provided.

11 Claims, 2 Drawing Sheets

PHARMACEUTICAL COMPOSITIONS OF NEAR IR CLOSED CHAIN, SULFO-CYANINE DYES

BACKGROUND OF THE INVENTION

Minimally invasive medical techniques are intended to reduce the amount of extraneous tissue that is damaged during diagnostic or surgical procedures, thereby reducing patient recovery time, discomfort, and deleterious side effects. While millions of "open" or traditional surgeries are performed each year in the United States; many of these surgeries can potentially be performed in a minimally invasive manner. One effect of minimally invasive surgery, for example, is reduced post-operative recovery time and related hospital stay. Because the average hospital stay for a standard surgery is typically significantly longer than the average stay for an analogous minimally invasive surgery, increased use of minimally invasive techniques could save millions of dollars in hospital costs each year. While many of the surgeries performed in the United States could potentially be performed in a minimally invasive manner, only a portion currently employ these techniques due to instrument limitations, method limitations, and the additional surgical training involved in mastering the techniques.

Minimally invasive tele-surgical systems are being developed to increase a surgeon's dexterity as well as to allow a surgeon to operate on a patient from a remote location. Telesurgery is a general term for surgical systems where the surgeon uses some form of remote control, e.g., a servo-mechanism, or the like, to manipulate surgical instrument movements rather than directly holding and moving the instruments by hand. In such a telesurgery system, the surgeon is provided with an image of the surgical site at the remote location. While viewing the surgical site on a suitable viewer or display, the surgeon performs the surgical procedures on the patient by manipulating master control input devices, which in turn control the motion of instruments. These input devices can move the working ends of the surgical instruments with sufficient dexterity to perform quite intricate surgical tasks.

Minimally invasive medical techniques, including tele-surgical systems can be further aided by improving visualization of the tissue where the procedure is to be carried out. One way to improve visualization of tissue is through the use of dyes. Thus, there is a need for novel, sterile, and non-toxic pharmaceutical compositions of near IR, closed chain, sulfo-cyanine dyes and methods for the visualization of tissue under illumination with near-infrared radiation. Surprisingly, the present invention meets these and other needs.

BRIEF SUMMARY OF THE INVENTION

The present invention generally provides novel, sterile, and non-toxic pharmaceutical compositions of near IR, closed chain, sulfo-cyanine dyes and methods for the visualization of tissue under illumination with near-infrared radiation.

In a first embodiment, the present invention provides a sterile pharmaceutical composition comprising a unit dosage form of a compound having the formula:

(I)

wherein,
$R^1$, $R^2$, $R^3$, and $R^4$ are each independently hydrogen, $C_{1-3}$ alkyl, or $-CO_2T$;
X is a single bond, $-O-$, or $-S-$;
subscripts a, b, c, and d are each independently an integer from 1 to 6, and
T is a metal ion, H, or a negative charge;
wherein, the composition is sterile, non-toxic, and adapted for administration to a patient for visualization of tissue under illumination with near-infrared radiation; and
wherein, the unit dosage form of the compound delivers to the patient an amount between 0.05 and 8 mg/kg.

In some cases, the composition has the formula:

(II)

wherein,
$R^1$, $R^2$, $R^3$, and $R^4$ are each independently hydrogen, $-CH_3$, or $-CO_2T$.

In some cases, the composition has the formula:

(III)

In some cases, the composition unit dosage form delivers to the patient the amount of 0.05, 0.10, 0.20, 0.30, 0.35, 0.40, 0.45, 0.50, 0.55, 0.60, 0.65, 0.70, 0.75, 0.80, 0.90, 1, 2, 4, 6, or 8 mg/kg.

In some cases, the composition is adapted for administration to a human patient to obtain visualization of human tissue under illumination with near-infrared radiation wherein the unit dosage form delivers to the patient an amount between 0.05 and 8 mg/kg. In some cases, the composition is dry and a single dose form.

In some cases the composition is lyophilized in a sterile container. In some cases, the composition is contained within a sterile container, where the container has a machine detectable identifier which is readable by a medical device.

In some cases, the composition further comprises combination with pharmaceutically acceptable excipients in an oral dosage form. In some cases, the composition further comprises combination with pharmaceutically acceptable carriers in an injectable dosage form. In some cases, the composition further comprises combination with pharmaceutically acceptable excipients in a dosage form for direct application to a surgical site.

In some embodiments, the present invention provides a use of the composition adapted for administration to a patient to obtain visualization of tissue under illumination with near-infrared radiation wherein the unit dosage form delivers to the patient an amount between 0.05 and 8 mg/kg. In some cases, the use is adapted for administration to a human patient to obtain visualization of human tissue under illumination with near-infrared radiation wherein the unit dosage form delivers to the patient an amount between 0.05 and 8 mg/kg.

In some embodiments, the present invention provides a method for visualization of tissue, the method comprising administering the composition to a patient, imaging the tissue under illumination with near-infrared radiation, and obtaining at least one image of tissue from the patient using the composition. In some cases, the method further comprises obtaining the image during administration, after administration, or both during and after administration of the composition.

In some cases, the method further comprises intravenously injecting the composition into a patient. In some cases, the composition is injected into a circulatory system.

In some cases, the method further comprises visualizing a patient area on which surgery is or will be performed, or for viewing a patient area otherwise being examined by a medical professional. In some cases, the method further comprises performing a surgical procedure on the patient areas based on the visualization of the surgical area. In some cases, the method further comprises viewing a patient area on which an ophthalmic, arthroscopic, laparoscopic, cardiothoracic, muscular, reconstructive, or neuro procedure is or will be performed. In some cases, the method further comprises obtaining ex vivo images of at least a portion of the patient.

BRIEF DESCRIPTION OF THE DRAWINGS

FIGS. 2A and 2B show the ureter of a pig after injection of a composition of formula III.

DETAILED DESCRIPTION OF THE INVENTION

I. General

The present invention provides novel, sterile, and non-toxic pharmaceutical compositions of near IR, closed chain, sulfo-cyanine dyes and methods for the visualization of tissue under illumination with near-infrared radiation.

II. Definitions

The abbreviations used herein have their conventional meaning within the chemical and biological arts.

The term "metal ion" as used herein refers to elements of the periodic table that are metallic and that are positively charged as a result of having fewer electrons in the valence shell than is present for the neutral metallic element. Metals that are useful in the present invention include metals capable of forming pharmaceutically acceptable compositions. Useful metals include Li, Na, K, Rb, Cs, Be, Mg, Ca, Sr, and Ba. One of skill in the art will appreciate that the metals described above can each adopt several different oxidation states. In some instances, the most stable oxidation state is formed, but other oxidation states are useful in the present invention.

As used herein, the term "sterile" refers to a system or components of a system free of infectious agents including bacteria, viruses, and bioactive DNA.

As used herein, the term "non-toxic" refers to the non-occurrence of detrimental effects when administered to a vertebrate as a result of using a pharmaceutical composition at levels effective for visualization of tissue under illumination with near-infrared radiation (therapeutic levels).

The term "unit dosage form" as used herein encompasses any measured amount that can suitably be used for administering a pharmaceutical composition to a patient. Preferably, the unit dosage form delivers to the patient an amount between 0.05 and 8 mg/kg, or 0.05 and 5 mg/kg, or 0.05 and 1 mg/kg. Suitable dosage ranges delivered to the patient also include 0.05, 0.10, 0.20, 0.30, 0.35, 0.40, 0.45, 0.50, 0.55, 0.60, 0.65, 0.70, 0.75, 0.80, 0.90, 1, 2, 4, 6, or 8 mg/kg. As recognized by those skilled in the art, when another form (e.g., another salt the pharmaceutical composition) is used in the formulation, the weight can be adjusted to provide an equivalent amount of the pharmaceutical composition.

As used herein, the term "visualization" refers to methods of obtaining graphic images of tissue by any means, including illumination with near-infrared radiation.

As used herein, the term "patient" denotes a mammal, such as a rodent, a feline, a canine, and a primate; most preferably said patient is a human.

The term "tissue" as used herein includes, but is not limited to, allogenic or xenogenic bone, neural tissue, fibrous connective tissue including tendons and ligaments, cartilage, dura, fascia, pericardia, muscle, heart valves, veins and arteries and other vessels, dermis, adipose tissue, or glandular tissue.

The term "oral dosage form" as used herein refers to its normal meaning in the art (i.e., a pharmaceutical composition in the form of a tablet, capsule, caplet, gelcap, geltab, pill and the like).

The term "injectable dosage form" as used herein refers to its normal meaning in the art (i.e., refer to a pharmaceutical composition in the form of solutions, suspensions, and emulsions, for example, water or water/propylene glycol solutions.)

"Pharmaceutically acceptable excipient" and "pharmaceutically acceptable carrier" refer to a substance that aids the administration of an active agent to and absorption by a patient and can be included in the compositions of the present invention without causing a significant adverse toxicological effect on the patient. Non-limiting examples of pharmaceutically acceptable excipients include water, NaCl, normal saline solutions, lactated Ringer's, normal sucrose, normal glucose, binders, fillers, disintegrants, lubricants, coatings, sweeteners, flavors and colors, and the like. One of skill in the art will recognize that other pharmaceutical excipients are useful in the present invention. Pharmaceutically acceptable carriers include but not limited to any adjuvants, excipients, glidants, sweeteners, diluents, preservatives, dyes/colorants, flavoring agents, surfactants, wetting agents, dispersing agents, suspending agents, stabilizing agents, isotonic agents, solvents or emulsors.

III. Pharmaceutical Compositions

A. Compounds

The compounds of the present invention comprise dyes of formulas I and II which absorb light at wavelengths in the near-infrared regions of the electromagnetic spectrum. References herein to the optionally plural term "wavelength(s)" indicates that the radiation may be a single wavelength or a spectrum of radiation having differing wavelengths.

In some embodiments, the present invention provides a sterile pharmaceutical composition comprising a unit dosage form of a compound having the formula:

(I)

wherein, $R^1$, $R^2$, $R^3$, and $R^4$ are each independently hydrogen, $C_{1-3}$ alkyl, or —$CO_2T$;

X is a single bond, —O—, or —S—;

subscripts a, b, c, and d are each independently an integer from 1 to 6, and T is a metal ion, H, or a negative charge;

wherein, the composition is sterile, non-toxic, and adapted for administration to a patient for visualization of tissue under illumination with near-infrared radiation; and wherein, the unit dosage form of the compound delivers to the patient an amount between 0.05 and 8 mg/kg.

In some other embodiments, the composition has the formula:

(II)

wherein, $R^1$, $R^2$, $R^3$, and $R^4$ are each independently hydrogen, —$CH_3$, or —$CO_2T$.

In some other embodiments, the composition has the formula:

(III)

In some cases, the composition is adapted for administration to a human patient to obtain visualization of human tissue under illumination with near-infrared radiation wherein the unit dosage form delivers to the patient an amount between 0.05 and 8 mg/kg. In some cases, the composition is dry and a single dose form.

In some cases the composition is lyophilized in a sterile container. In some cases, the composition is contained within a sterile container, where the container has a machine detectable identifier which is readable by a medical device.

In some cases, the composition further comprises combination with pharmaceutically acceptable excipients in an oral dosage form. In some cases, the composition further comprises combination with pharmaceutically acceptable carriers in an injectable dosage form. In some cases, the composition further comprises combination with pharmaceutically acceptable excipients in a dosage form for direct application to a surgical site.

The compounds of the present invention may exist as salts. The present invention includes such salts. Examples of applicable salt forms include hydrochlorides, hydrobromides, sulfates, methanesulfonates, nitrates, maleates, acetates, citrates, fumarates, tartrates (eg (+)-tartrates, (−)-tartrates or mixtures thereof including racemic mixtures, succinates, benzoates and salts with amino acids such as glutamic acid. These salts may be prepared by methods known to those skilled in art. Also included are base addition salts such as sodium, potassium, calcium, ammonium, organic amino, or magnesium salt, or a similar salt. When compounds of the present invention contain relatively basic functionalities, acid addition salts can be obtained by contacting the neutral form of such compounds with a sufficient amount of the desired acid, either neat or in a suitable inert solvent. Examples of acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from organic acids like acetic, propionic, isobutyric, maleic, malonic, benzoic, succinic, suberic, fumaric, lactic, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like. Certain specific compounds of the present invention contain both basic and acidic functionalities that allow the compounds to be converted into either base or acid addition salts.

Other salts include acid or base salts of the compounds used in the methods of the present invention. Illustrative examples of pharmaceutically acceptable salts are mineral acid (hydrochloric acid, hydrobromic acid, phosphoric acid, and the like) salts, organic acid (acetic acid, propionic acid, glutamic acid, citric acid and the like) salts, and quaternary ammonium (methyl iodide, ethyl iodide, and the like) salts. It is understood that the pharmaceutically acceptable salts are non-toxic. Additional information on suitable pharmaceutically acceptable salts can be found in Remington's Pharmaceutical Sciences, 17th ed., Mack Publishing Company, Easton, Pa., 1985, which is incorporated herein by reference.

Pharmaceutically acceptable salts include salts of the active compounds which are prepared with relatively non-toxic acids or bases, depending on the particular substituents found on the compounds described herein. When compounds of the present invention contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds of the present invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively non-toxic organic acids like acetic, propionic, isobutyric, maleic, malonic, benzoic, succinic, suberic, fumaric, lactic, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, for example, Berge et al., "Pharmaceutical Salts", Journal of Pharmaceutical Science, 1977, 66, 1-19). Certain specific compounds of the present invention contain both basic and acidic functionalities that allow the compounds to be converted into either base or acid addition salts.

The neutral forms of the compounds are preferably regenerated by contacting the salt with a base or acid and isolating the parent compound in the conventional manner. The parent form of the compound differs from the various salt forms in certain physical properties, such as solubility in polar solvents.

Certain compounds of the present invention can exist in unsolvated forms as well as solvated forms, including hydrated forms. In general, the solvated forms are equivalent to unsolvated forms and are encompassed within the scope of the present invention. Certain compounds of the present invention may exist in multiple crystalline or amorphous forms. In general, all physical forms are equivalent for the uses contemplated by the present invention and are intended to be within the scope of the present invention.

In some embodiments, the present invention provides a pharmaceutical composition including a pharmaceutically acceptable excipient.

B. Synthesis

Exemplary syntheses of the compounds in the pharmaceutical compositions of the present invention are described in U.S. Pat. Nos. 6,887,854 and 6,159,657 and are incorporated herein in their entirety. For example, the synthesis of the compounds in the pharmaceutical compositions of the present invention can proceed as follows:

-continued

Additionally, some compounds in the pharmaceutical compositions of the present invention are commercially available, including DyLight 800 (ThermoFisher).

C. Formulation

The compositions of the present invention can be prepared in a wide variety of oral, parenteral and topical dosage forms. Oral preparations include tablets, pills, powder, dragees, capsules, liquids, lozenges, cachets, gels, syrups, slurries, suspensions, etc., suitable for ingestion by the patient. The compositions of the present invention can also be administered by injection, that is, intravenously, intramuscularly, intracutaneously, subcutaneously, intraduodenally, or intraperitoneally. Also, the compositions described herein can be administered by inhalation, for example, intranasally. Additionally, the compositions of the present invention can be administered transdermally. The compositions of this invention can also be administered by intraocular, insufflation, powders, and aerosol formulations (for examples of steroid inhalants, see Rohatagi, J. Clin. Pharmacol. 35:1187-1193, 1995; Tjwa, Ann. Allergy Asthma Immunol. 75:107-111, 1995). Accordingly, the present invention also provides pharmaceutical compositions including a pharmaceutically acceptable carrier or excipient.

For preparing pharmaceutical compositions from the present invention, pharmaceutically acceptable carriers can be either solid or liquid. Solid form preparations include powders, tablets, pills, capsules, cachets, suppositories, and dispersible granules. A solid carrier can be one or more substances, which may also act as diluents, flavoring agents, binders, preservatives, tablet disintegrating agents, or an encapsulating material. Details on techniques for formulation and administration are well described in the scientific and patent literature, see, e.g., the latest edition of Remington's Pharmaceutical Sciences, Maack Publishing Co, Easton Pa. ("Remington's").

In powders, the carrier is a finely divided solid, which is in a mixture with the finely divided active component. In tablets, the active component is mixed with the carrier having the necessary binding properties in suitable proportions and compacted in the shape and size desired. The powders and tablets preferably contain from 5% or 10% to 70% of the compounds of the present invention.

Suitable solid excipients include, but are not limited to, magnesium carbonate; magnesium stearate; talc; pectin; dextrin; starch; tragacanth; a low melting wax; cocoa butter; carbohydrates; sugars including, but not limited to, lactose, sucrose, mannitol, or sorbitol, starch from corn, wheat, rice, potato, or other plants; cellulose such as methyl cellulose, hydroxypropylmethyl-cellulose, or sodium carboxymethylcellulose; and gums including arabic and tragacanth; as well as proteins including, but not limited to, gelatin and collagen. If desired, disintegrating or solubilizing agents may be added, such as the cross-linked polyvinyl pyrrolidone, agar, alginic acid, or a salt thereof, such as sodium alginate.

Dragee cores are provided with suitable coatings such as concentrated sugar solutions, which may also contain gum arabic, talc, polyvinylpyrrolidone, carbopol gel, polyethylene glycol, and/or titanium dioxide, lacquer solutions, and suitable organic solvents or solvent mixtures. Dyestuffs or pigments may be added to the tablets or dragee coatings for product identification or to characterize the quantity of active compound (i.e., dosage). Pharmaceutical compositions of the invention can also be used orally using, for example, push-fit capsules made of gelatin, as well as soft, sealed capsules made of gelatin and a coating such as glycerol or sorbitol. Push-fit capsules can contain the compositions of the present invention mixed with a filler or binders such as lactose or starches, lubricants such as talc or magnesium stearate, and, optionally, stabilizers. In soft capsules, the compositions of the present invention may be dissolved or suspended in suitable liquids, such as fatty oils, liquid paraffin, or liquid polyethylene glycol with or without stabilizers.

Liquid form preparations include solutions, suspensions, and emulsions, for example, water or water/propylene glycol solutions. For parenteral injection, liquid preparations can be formulated in solution in aqueous polyethylene glycol solution.

Aqueous solutions suitable for oral use can be prepared by dissolving the compositions of the present invention in water and adding suitable colorants, flavors, stabilizers, and thickening agents as desired. Aqueous suspensions suitable for oral use can be made by dispersing the finely divided active component in water with viscous material, such as natural or synthetic gums, resins, methylcellulose, sodium carboxymethylcellulose, hydroxypropylmethylcellulose, sodium alginate, polyvinylpyrrolidone, gum tragacanth and gum acacia, and dispersing or wetting agents such as a naturally occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethylene oxycetanol), a condensation product of ethylene oxide with a partial ester derived from a fatty acid and a hexitol (e.g., polyoxyethylene sorbitol mono-oleate), or a condensation product of ethylene oxide with a partial ester derived from fatty acid and a hexitol anhydride (e.g., polyoxyethylene sorbitan mono-oleate). The aqueous suspension can also contain one or more preservatives such as ethyl or n-propyl p-hydroxybenzoate, one or more coloring agents, one or more flavoring agents and one or more sweetening agents, such as sucrose, aspartame or saccharin. Formulations can be adjusted for osmolarity.

Also included are solid form preparations, which are intended to be converted, shortly before use, to liquid form preparations for oral administration. Such liquid forms include solutions, suspensions, and emulsions. These preparations may contain, in addition to the active component, colorants, flavors, stabilizers, buffers, artificial and natural sweeteners, dispersants, thickeners, solubilizing agents, and the like.

Oil suspensions can be formulated by suspending the compositions of the present invention in a vegetable oil, such as arachis oil, olive oil, sesame oil or coconut oil, or in a mineral oil such as liquid paraffin; or a mixture of these. The oil suspensions can contain a thickening agent, such as beeswax, hard paraffin or cetyl alcohol. Sweetening agents can be added to provide a palatable oral preparation, such as glycerol, sorbitol or sucrose. These formulations can be preserved by the addition of an antioxidant such as ascorbic acid. As an example of an injectable oil vehicle, see Minto, J. Pharmacol. Exp. Ther. 281:93-102, 1997. The pharmaceutical formulations of the invention can also be in the form of oil-in-water emulsions. The oily phase can be a vegetable oil or a mineral oil, described above, or a mixture of these. Suitable emulsifying agents include naturally-occurring gums, such as gum acacia and gum tragacanth, naturally occurring phosphatides, such as soybean lecithin, esters or partial esters derived from fatty acids and hexitol anhydrides, such as sorbitan mono-oleate, and condensation products of these partial esters with ethylene oxide, such as polyoxyethylene sorbitan mono-oleate. The emulsion can also contain sweetening agents and flavoring agents, as in the formulation of syrups and elixirs. Such formulations can also contain a demulcent, a preservative, or a coloring agent.

The compositions of the present invention can also be delivered as microspheres for slow release in the body. For example, microspheres can be formulated for administration via intradermal injection of drug-containing microspheres, which slowly release subcutaneously (see Rao, J. Biomater Sci. Polym. Ed. 7:623-645, 1995; as biodegradable and injectable gel formulations (see, e.g., Gao Pharm. Res. 12:857-863, 1995); or, as microspheres for oral administration (see, e.g., Eyles, J. Pharm. Pharmacol. 49:669-674, 1997). Both transdermal and intradermal routes afford constant delivery for weeks or months.

In another embodiment, the compositions of the present invention can be formulated for parenteral administration, such as intravenous (IV) administration or administration into a body cavity or lumen of an organ. The formulations for administration will commonly comprise a solution of the compositions of the present invention dissolved in a pharmaceutically acceptable carrier. Among the acceptable vehicles and solvents that can be employed are water and Ringer's solution, an isotonic sodium chloride. In addition, sterile fixed oils can conventionally be employed as a solvent or suspending medium. For this purpose any bland fixed oil can be employed including synthetic mono- or diglycerides. In addition, fatty acids such as oleic acid can likewise be used in the preparation of injectables. These solutions are sterile and generally free of undesirable matter. These formulations may be sterilized by conventional, well known techniques including radiation, chemical, heat/pressure, and filtration sterilization techniques. The formulations may contain pharmaceutically acceptable auxiliary substances as required to approximate physiological conditions such as pH adjusting and buffering agents, toxicity adjusting agents, e.g., sodium acetate, sodium chloride, potassium chloride, calcium chloride, sodium lactate and the like. The concentration of the compositions of the present invention in these formulations can vary widely, and will be selected primarily based on fluid volumes, viscosities, body weight, and the like, in accordance with the particular mode of administration selected and the patient's needs. For IV administration, the formulation can be a sterile injectable preparation, such as a sterile injectable aqueous or oleaginous suspension. This suspension can be formulated according to the known art using those suitable dispersing or wetting agents and suspending agents. The sterile injectable preparation can also be a sterile injectable solution or suspension in a non-toxic parenterally-acceptable diluent or solvent, such as a solution of 1,3-butanediol.

In another embodiment, the formulations of the compositions of the present invention can be delivered by the use of liposomes which fuse with the cellular membrane or are endocytosed, i.e., by employing ligands attached to the liposome, or attached directly to the oligonucleotide, that bind to surface membrane protein receptors of the cell resulting in endocytosis. By using liposomes, particularly where the liposome surface carries ligands specific for target cells, or are otherwise preferentially directed to a specific organ, one can focus the delivery of the compositions of the present invention into the target cells in vivo. (See, e.g., Al-Muhammed, J. Microencapsul. 13:293-306, 1996; Chonn, Curr. Opin. Biotechnol. 6:698-708, 1995; Ostro, Am. J. Hosp. Pharm. 46:1576-1587, 1989).

Lipid-based drug delivery systems include lipid solutions, lipid emulsions, lipid dispersions, self-emulsifying drug delivery systems (SEDDS) and self-microemulsifying drug delivery systems (SMEDDS). In particular, SEDDS and SMEDDS are isotropic mixtures of lipids, surfactants and co-surfactants that can disperse spontaneously in aqueous media and form fine emulsions (SEDDS) or microemulsions (SMEDDS). Lipids useful in the formulations of the present invention include any natural or synthetic lipids including, but not limited to, sesame seed oil, olive oil, castor oil, peanut oil, fatty acid esters, glycerol esters, Labrafil®, Labrasol®, Cremophor®, Solutol®, Tween®, Capryol®, Capmul®, Captex®, and Peceol®.

The compositions of the present invention are sterile and generally free of undesirable matter. The compounds and compositions may be sterilized by conventional, well known techniques including heat/pressure, gas plasma, steam, radiation, chemical, and filtration sterilization techniques.

For example, terminal heat sterilization can be used to destroy all viable microorganisms within the final formulation. An autoclave is commonly used to accomplish terminal heat-sterilization of drug products in their final packaging. Typical autoclave cycles in the pharmaceutical industry to achieve terminal sterilization of the final product are 121° C. for 15 minutes. The compositions of the present invention can be autoclaved at a temperature ranging from 115 to 130° C. for a period of time ranging from 5 to 40 minutes with acceptable stability. Autoclaving is preferably carried out in the temperature range of 119 to 122° C. for a period of time ranging from 10 to 36 minutes.

The compositions can also be sterilized by dry heat as described by Karlsson, et al., in U.S. Pat. No. 6,392,036, which discloses a method for the dry heat sterilization that can be used for drug formulations. The compositions can also be sterilized as described in WO 02/41925 to Breath Limited, which discloses a rapid method, similar to pasteurization, for the sterilization of compositions. This method entails pumping the composition to be sterilized through stainless steel pipes and rapidly raising the temperature of the composition to about 130-145° C. for about 2-20 seconds, subsequently followed by rapid cooling in seconds to ambient conditions.

The compositions can also be sterilized by irradiation as described by Illum and Moeller in *Arch. Pharm. Chemi. Sci.*, Ed. 2, 1974, pp. 167-174). The compositions can also be sterilized by UV, x-rays, gamma rays, e beam radiation, flaming, baking, and chemical sterilization.

Alternatively, sterile pharmaceutical compositions according to the present invention may be prepared using aseptic processing techniques. Aseptic filling is ordinarily used to prepare drug products that will not withstand heat sterilization, but in which all of the ingredients are sterile. Sterility is maintained by using sterile materials and a controlled working environment. All containers and apparatus are sterilized, preferably by heat sterilization, prior to filling. The container (e.g., vial, ampoule, infusion bag, bottle, or syringe) are then filled under aseptic conditions.

The compounds and compositions of the present invention are non-toxic and generally free of detrimental effects when administered to a vertebrate at levels effective for visualization of tissue under illumination with near-infrared radiation. Toxicity of the compounds and compositions of the present invention can be assessed by measuring their effects on a target (organism, organ, tissue or cell). Because individual targets typically have different levels of response to the same dose of a compound, a population-level measure of toxicity is often used which relates the probabilities of an outcome for a given individual in a population. Toxicology of compounds can be determined by conventional, well known techniques including in vitro (outside of a living organism) and in vivo (inside of a living organism) studies.

For example, determination of metabolic stability is commonly examined when assessing the toxicity of a compound as it is one of several major determinates in defining the oral bioavailability and systemic clearance of a compound. After a compound is administered orally, it first encounters metabolic enzymes in the gastrointestinal lumen as well as in the intestinal epithelium. After it is absorbed into the bloodstream through the intestinal epithelium, it is first delivered to the liver via the portal vein. A compound can be effectively cleared by intestinal or hepatic metabolism before it reaches systemic circulation, a process known as first pass metabolism. The stability of a compound towards metabolism within the liver as well as extrahepatic tissues will ultimately determine the concentration of the compound found in the systemic circulation and affect its half-life and residence time within the body. Cytochrome P450 (CYP) enzymes are found primarily in the liver but also in the intestinal wall, lungs, kidneys and other extrahepatic organs and are the major enzymes involved in compound metabolism. Many compounds undergo deactivation by CYPs, either directly or by facilitated excretion from the body. Also, many compounds are bioactivated by CYPs to form their active compounds. Thus, determining the reactivity of a compound to CYP enzymes is commonly used to assess metabolic stability of a compound.

The Ames reverse mutation Assay is another common toxicology assay for assessing the toxicity of a compound. The Ames Assay, utilizes several different tester strains, each with a distinct mutation in one of the genes comprising the histidine (his) biosynthetic operon (Ames, B. N., et al., (1975) Mutation Res. 31:347-363). The detection of revertant (i.e., mutant) bacteria in test samples that are capable of growth in the absence of histidine indicates that the compound under evaluation is characterized by genotoxic (i.e. mutagenic) activity. The Ames Assay is capable of detecting several different types of mutations (genetic damage) which may occur in one or more of the tester strains. The practice of using an in vitro bacterial assay to evaluate the genotoxic activity of drug candidates is based on the prediction that a substance that is mutagenic in a bacterium is likely to be carcinogenic in laboratory animals, and by extension may be carcinogenic or mutagenic to humans.

In addition, the human ether-a-go-go related gene (hERG) assay can be used to evaluate the potential cardiotoxicity of a compound. Cardiotoxicity can arise when the QT interval is prolonged leading to an elevated risk of life-threatening arrhythmias. The QT interval is a measure of the time between the start of the Q wave and the end of the T wave in the heart's electrical cycle. The QT interval represents electrical depolarization and repolarization of the ventricles. A lengthened QT interval has most commonly been associated with loss of current through hERG potassium ion channels due to direct block of the ion channel by drugs or by inhibition of the plasma membrane expression of the channel protein (Su et al. J. Biomol Screen 2011, 16, 101-111). Thus, an in vitro hERG screening assay can be used to detect disruption or inhibition of the hERG membrane trafficking function and assess potential cardiotoxicity of a compound.

Other methods of assessing the toxicity of compounds include in vivo studies which administer relatively large doses of a test compound to a group of animals to determine the level which is lethal to a percentage of the population (mean lethal dose $LD_{50}$ or mean lethal concentration $LC_{50}$). Toxicity of a compound can also be assessed in vivo by examining whether a compound produces statistically significant negative effects on cardiac, blood pressure, central nervous system (CNS), body weight, food intake, gross or microscopic pathology, clinical pathology, or respiratory measures in an animal.

For example, in a set of in vitro studies evaluating the metabolic stability of a composition of formula III, it was shown that the compound appears to be stable in rat, dog and human plasma, does not appear to be broken down into metabolites, and does not show any significant reactivity to 9 major CYP liver enzymes. Additionally, the composition of formula III does not show any mutagenicity at any of the tested doses in the Ames reverse mutation assay, a widely used in vitro method that determines the ability of a chemical to cause mutations in DNA. Further safety pharmacology was assessed in vitro using the human ether-a-go-go related gene (hERG) assay for determining possible cardio-toxic effects. Studies utilizing this assay determined that the composition of formula III shows only a small (11%) inhibition of hERG function at the highest tested concentration (30 times higher than levels effective for visualization), indicating even at this concentration the composition of formula III is unlikely to translate into any clinically threatening physiological cardiac changes.

Furthermore, toxicology of the composition of formula III was also investigated in non-clinical in vivo studies in both rats and dogs. A study evaluating the effects of the composition of formula III on cardiac and respiratory safety in radio-telemetry monitored dogs showed no statistically significant negative effects on cardiac, blood pressure or respiratory measures at doses up to 80 times higher than those required for visualization. Additional safety pharmacology performed over 28 days in rats indicated doses as high as 160 times visualization levels per day showed no biologically meaningful effects on the central nervous system (CNS). Finally, a series of toxicology studies in dogs showed doses as high as 100 times visualization levels showed no significant effects on body weight, food intake, gross or microscopic pathology as well as clinical pathology (clinical serum chemistry, hematology, coagulation and urinalysis). No mortality was observed at any tested dose of the composition of formula III in rat, dog or pig animal models.

In some embodiments, the compositions of the present invention can be lyophilized in a sterile container for convenient dry storage and transport. A ready-to-use preparation can subsequently be made by reconstituting the lyophilized compositions with sterile water. The terms "lyophilization," "lyophilized," and "freeze-dried" refer to a process by which the material to be dried is first frozen and then the ice or frozen solvent is removed by sublimation in a vacuum environment. An excipient may be included in pre-lyophilized formulations to enhance stability of the lyophilized product upon storage.

In some embodiments, the composition can be contained within a sterile container, where the container has a machine detectable identifier which is readable by a medical device. As used herein, "machine detectable identifier" includes identifiers visible or detectable by machines including medical devices. In some instances, the medical device is a tele-surgical system. Machine detectable identifiers may facilitate the access or utilization of information that is directly encoded in the machine detectable identifier, or stored elsewhere. Examples of machine detectable identifiers include microchips, radio frequency identification (RFID) tags, barcodes (e.g., 1-dimensional or 2-dimensional barcode), data matrices, quick-response (QR) codes, and holograms. One of skill in the art will recognize that other machine detectable identifiers are useful in the present invention.

In some cases, the machine detectable identifier can include a microchip, an integrated circuit (IC) chip, or an electronic signal from a microchip which is detectable and/or readable by a computer system which is in communication with the medical device. In some cases, the machine detectable identifier includes a radio frequency identification (RFID) tag. RFID tags are sometimes called as transponders. RFID tags generally are devices formed of an IC chip, an antenna, an adhesive material, and are used for transmitting or receiving predetermined data with an external reader or interrogator. RFID tags can transmit or receive data with a reader by using a contactless method. According to the amplitude of a used frequency, inductive coupling, backscattering, and surface acoustic wave (SAW) may be used. Using electromagnetic waves, data may be transmitted or received to or from a reader by using a full duplex method, a half duplex (HDX) method, or a sequential (SEQ) method.

In some cases, the machine detectable identifier can include a barcode. Barcodes include any machine-readable format, including one-dimensional and two-dimensional formats. One-dimensional formats include, for example, Universal Product Code (UPC) and Reduced Space Symbology (RSS). Two-dimensional formats, or machine-readable matrices, include for example, Quick Response (QR) Code and Data Matrix.

In some cases, the medical device can be configured to detect the machine detectable identifier. In one example, the medical device is a tele-surgical system that includes a special imaging mode (e.g., a fluorescence imaging mode) for use with dyes such as those described in this disclosure. One example of a tele-surgical system that includes a fluorescence imaging mode is described in U.S. Pat. No. 8,169,468, entitled "Augmented Stereoscopic Visualization for a Surgical Robot," which is hereby incorporated in its entirety herein. In some cases, medical devices can incorporate an imaging device that can scan, read, view, or otherwise detect a machine detectable identifier that is displayed to the imaging device. In one aspect, the medical device will permit a user to access the fluorescence imaging mode of the medical device only if the medical device detects the presence of a known machine detectable identifier that corresponds to a dye identified as being compatible for use with the medical device. In contrast, if the medical device does not detect a known machine detectable identifier, the medical device will not permit a user to access the fluorescence imaging mode and associated functionality. Imaging devices can include optical scanners, barcode readers, cameras, and imaging devices contained within a tele-surgical system such as an endoscope. Information associated with the machine detectable identifier can then be retrieved by the medical device using an imaging device. Upon detection of the identifier, an automatic process may be launched to cause a predetermined action to occur, or certain data to be retrieved or accessed. The information encoded onto the machine detectable identifier may include instructions for triggering an action, such as administering a composition of the present invention to a patient. In some embodiments, the machine detectable identifier includes unencrypted e-pedigree information in the desired format. The e-pedigree information can include, for example, lot, potency, expiration, national drug code, electronic product code, manufacturer, distributor, wholesaler, pharmacy and/or a unique identifier of the salable unit.

In some embodiments, the sterile container having a machine detectable identifier includes a fluid outlet configured to mate with the medical device. In some cases, the fluid outlet of the machine detectable identifier is mechanically affixed to the medical device.

C. Administration

The compounds and compositions of the present invention can be delivered by any suitable means, including oral, parenteral and topical methods. Transdermal administration methods, by a topical route, can be formulated as applicator sticks, solutions, suspensions, emulsions, gels, creams, ointments, pastes, jellies, paints, powders, and aerosols.

The pharmaceutical preparation is preferably in unit dosage form. In such form the preparation is subdivided into unit doses containing appropriate quantities of the compounds and compositions of the present invention. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

In some embodiments, co-administration can be accomplished by co-formulation, i.e., preparing a single pharmaceutical composition including the compounds and compositions of the present invention and any other agent. Alternatively, the various components can be formulated separately.

The compositions of the present invention, and any other agents, can be present in any suitable amount, and can depend on various factors including, but not limited to, weight and age of the patient, state of the disease, etc. Suitable dosage ranges deliver to the patient an amount from about 0.05 and 8 mg/kg, or about 0.05 and 5 mg/kg, or about 0.05 and 1 mg/kg. Suitable dosage ranges also deliver to the patient the amount of 0.05, 0.10, 0.20, 0.30, 0.35, 0.40, 0.45, 0.50, 0.55, 0.60, 0.65, 0.70, 0.75, 0.80, 0.90, 1, 2, 4, 6, or 8 mg/kg.

The composition can also contain other compatible compositions. The compositions described herein can be used in combination with one another, with other active compositions known to be useful for visualization of tissue under illumination with near-infrared radiation, or with compositions that may not be effective alone, but may contribute to the efficacy of the active composition.

The terms and expressions which have been employed herein are used as terms of description and not of limitation, and there is no intention in the use of such terms and expressions of excluding equivalents of the features shown and described, or portions thereof, it being recognized that various modifications are possible within the scope of the invention claimed. Moreover, any one or more features of any embodiment of the invention may be combined with any one or more other features of any other embodiment of the invention, without departing from the scope of the invention.

All publications, patents, and patent applications cited herein are hereby incorporated by reference in their entirety for all purposes.

IV. Methods for Visualization of Tissue

The present invention generally provides novel, sterile, and non-toxic pharmaceutical compositions of near IR, closed chain, sulfo-cyanine dyes and methods for the visualization of tissue under illumination with near-infrared radiation.

In a first embodiment, the present invention provides a sterile pharmaceutical composition comprising a unit dosage form of a compound having the formula:

(I)

wherein, $R^1$, $R^2$, $R^3$, and $R^4$ are each independently hydrogen, $C_{1-3}$ alkyl, or —$CO_2T$;

X is a single bond, —O—, or —S—;

subscripts a, b, c, and d are each independently an integer from 1 to 6, and

T is a metal ion, H, or a negative charge;

wherein, the composition is sterile, non-toxic, and adapted for administration to a patient for visualization of tissue under illumination with near-infrared radiation; and wherein the unit dosage form of the compound delivers to the patient an amount between 0.05 and 8 mg/kg.

In some embodiments, the present invention provides a use of the composition adapted for administration to a patient to obtain visualization of tissue under illumination with near-infrared radiation wherein the unit dosage form delivers to the patient an amount between 0.05 and 8 mg/kg. In some cases, the use is adapted for administration to a human patient to obtain visualization of human tissue under illumination with near-infrared radiation wherein the unit dosage form delivers to the patient an amount between 0.05 and 8 mg/kg.

In some embodiments, the present invention provides a method for visualization of tissue, the method comprising administering the composition to a patient, imaging the tissue under illumination with near-infrared radiation, and obtaining at least one image of tissue from the patient using the composition. In some cases, the method further comprises obtaining the image during administration, after administration, or both during and after administration of the composition.

In some cases, the method further comprises intravenously injecting the composition into a patient. In some cases, the composition is injected into a circulatory system.

In some cases, the method further comprises visualizing a patient area on which surgery is or will be performed, or for viewing a patient area otherwise being examined by a medical professional. In some cases, the method further comprises performing a surgical procedure on the patient areas based on the visualization of the surgical area. In some cases, the method further comprises viewing a patient area on which an ophthalmic, arthroscopic, laparoscopic, cardiothoracic, muscular, or neuro procedure is or will be performed. In some cases, the method further comprises obtaining ex vivo images of at least a portion of the patient.

In some cases, the method further comprises the use of compositions of the present invention in combination with the da Vinci Surgical System's Firefly fluorescence, in providing an augmented view that enhances the difficult-to-visualize tissue to reduce the injury rate and possibly speed up surgery by providing the surgeon with confidence and security that he/she is not causing injury. Surgeons often have a difficult time locating the tubular structure known as the ureter, which carries urine from the kidneys to the bladder, during minimally invasive gynecologic procedures such as benign and malignant hysterectomy due to the method of approaching and visualizing the relevant anatomy. The incidence rate of ureteral injury is 1-3%, amounting to 5000-15000 women annually in the US. The injury rate is even higher in colorectal surgeries, on the order of 6-8% and the ureter is often cut if the surgeon does not take extreme care in doing a meticulous dissection. In cases with significant adhesions or fibrosis from prior surgeries, radiation therapy or other interventions, the task of identification can be much more difficult and time consuming. In complex urological cases such as pyeloplasty to relieve uretero-pelvic junction obstructions, visualization of the ureter can be difficult and an imaging agent such as compositions of the present invention can help the surgeon identify normal or aberrant anatomy.

V. Examples

Figure 1:
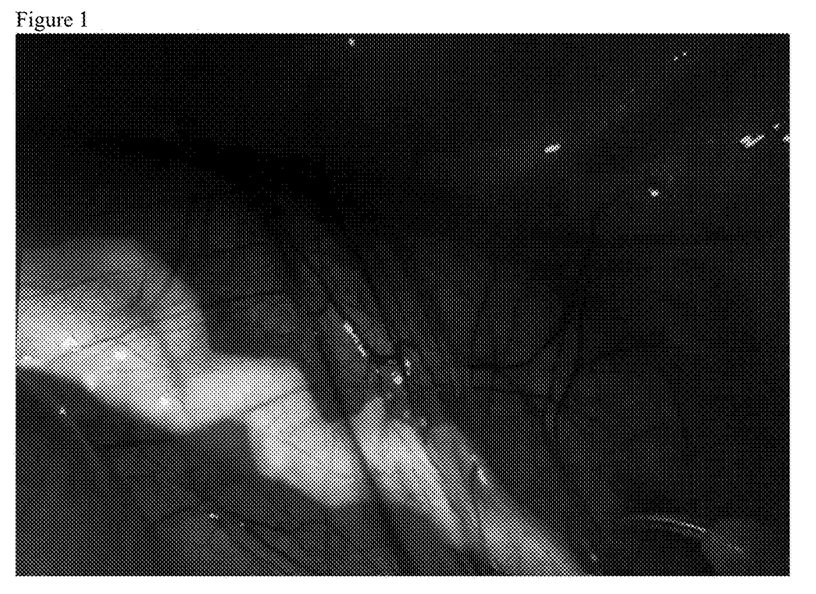
FIG. 1 shows the visualization of a ureter after injection of a composition of formula III on the da Vinci Surgical System upon excitation with near-infrared light in Firefly fluorescence mode. Upon conversion to greyscale images, quantification of infrared signal intensity of the kidney was measured in white light.
Figure 2A:
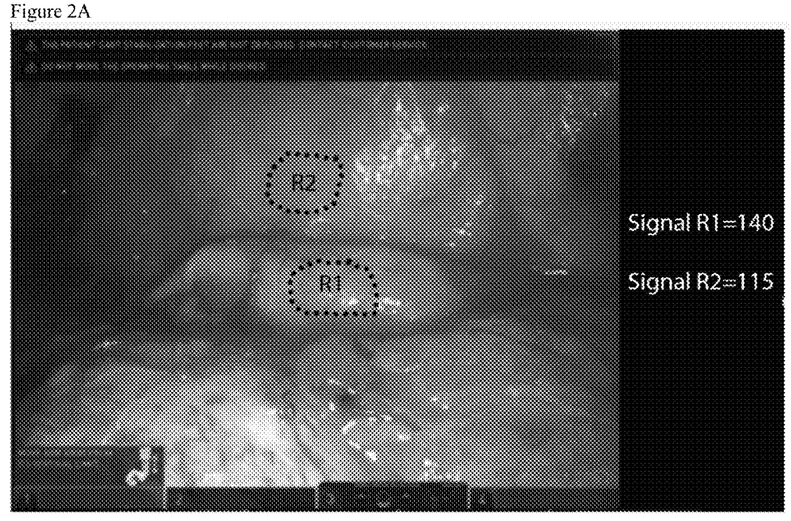
FIG. 2A shows white light visualization of the ureter of a pig after injection of a composition of formula III on the da Vinci Surgical System.
Figure 2B:
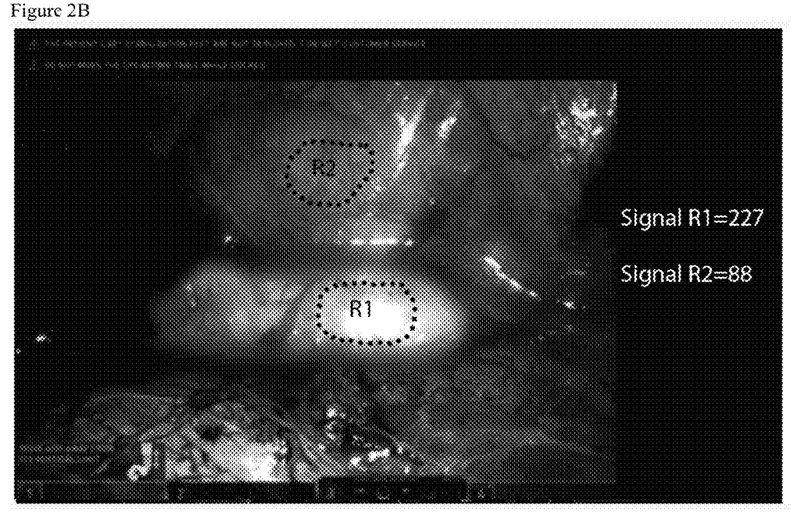
FIG. 2B shows visualization of the ureter of a pig after injection of the composition of formula III on the da Vinci Surgical System upon excitation with near-infrared light in Firefly fluorescence mode. Upon conversion to greyscale images, quantification of signal intensity of the ureter (R1, for Region 1) and background tissue (R2, for Region 2) were measured in the white light (no near infrared signal, FIG. 2A) and fluorescent (infrared signal present, FIG. 2B) images. The signal to background ratio, R1/R2 is 1.22 in the white light image and 2.58 in the fluorescent image.

Example 1. Visualization of Kidney and Ureter Under Illumination 20 mg of a compound of formula III in 10 ml of sterile water was administered intravenously to five pigs. Laparoscopic ports were placed and the da Vinci Surgical System was connected to the ports. The endoscope of the system was directed at the kidney of the pig, and laser excitation at approximately 800 nm was used to excite the composition of formula III within the ureter (FIG. 1). A small amount of blue and green light were also emitted in order to allow visualization of the background anatomy. Approximately 10 minutes after administration, the composition of formula III was seen exiting the kidney via the ureter, on its way to the bladder for excretion (FIGS. 2A and 2B).

Example 2. Visualization of Kidney and Ureter Under Illumination

An augmented view to enhance difficult-to-visualize kidneys ureters in a patient can be achieved by intravenously administering 20 mg of a compound of formula III in 10 ml of sterile water to a 60 kg human patient 15 minutes prior to desired visualization. The endoscope of the system can be directed at the kidney of the patient, and laser excitation at approximately 800 nm can be used to excite the composition of formula III within the ureter. A small amount of blue and green light can also be emitted in order to allow visualization of the background anatomy. Approximately 15 minutes after administration, visualization of the ureter can be achieved as the composition of formula III exits the kidney via the ureter, on its way to the bladder for excretion.

What is claimed is:

1. A method of visualizing tissue in a patient, the method comprising the step of administering a sterile pharmaceutical composition comprising a unit dosage form of a compound having the formula:

(I)

wherein,
$R^1$, $R^2$, $R^3$, and $R^4$ are each independently hydrogen, $C_{1-3}$ alkyl, or —$CO_2T$;
X is a single bond, —O—, or —S—;
subscripts a, b, c, and d are each independently an integer from 1 to 6, and
T is a metal ion, H, or a negative charge;
wherein the composition is non-toxic, and wherein the unit dosage form delivers to the patient an amount sufficient to visualize tissue; and further comprising imaging the tissue under illumination with near-infrared radiation, and obtaining at least one image of the tissue from the patient using the composition.

2. The method of claim 1 wherein the unit dosage form delivers to the patient an amount between 0.05 and 8 mg/kg.

3. The method of claim 1 further comprising obtaining the image during administration, after administration, or both during and after administration of the composition.

4. The method of claim 1 where the step of administering a sterile pharmaceutical composition is by intravenous injection.

5. The method of claim 1 where the composition is injected into a circulatory system.

6. The method of claim 1 further comprising visualizing a patient area on which surgery is or will be performed, or for viewing a patient area otherwise being examined by a medical professional.

7. The method of claim 6 further comprising performing a surgical procedure on the patient area based on the visualization of the surgical area.

8. The method of claim 6 further comprising viewing a patient area on which an ophthalmic, arthroscopic, laparoscopic, cardiothoracic, muscular, or neuro procedure is or will be performed.

9. The method of claim 1 further comprising obtaining ex vivo images of at least a portion of the patient.

10. The method of claim 1 wherein the compound has the formula:

(II)

wherein,
$R^1$, $R^2$, $R^3$, and $R^4$ are each independently hydrogen, —$CH_3$, or —$CO_2T$.

11. The method of claim 1 wherein the compound is:

(III)

* * * * *